United States Patent [19]
Hagberg et al.

[11] Patent Number: 4,752,483

[45] Date of Patent: Jun. 21, 1988

[54] METHOD FOR PRODUCING A HIGHLY FLAVORED CHEESE INGREDIENT

[75] Inventors: Elroy C. Hagberg, Pennsauken; Jay R. Haislip; Bobby R. Johnson, both of Cherry Hill, all of N.J.

[73] Assignee: Campbell Soup Company, Camden, N.J.

[21] Appl. No.: 869,049

[22] Filed: May 30, 1986

[51] Int. Cl.[4] .............................................. A23C 9/12
[52] U.S. Cl. ........................................ 426/35; 426/36; 426/582; 426/650; 426/589
[58] Field of Search ................ 426/34, 35, 36, 37-39, 426/40, 41-43, 61, 62, 63-64, 56, 582, 583, 580, 589, 650, 653, 652, 656-657

[56] References Cited

U.S. PATENT DOCUMENTS

| | | | |
|---|---|---|---|
| 2,225,553 | 12/1940 | Conquest | 99/151 |
| 2,343,713 | 3/1944 | Spur | 99/54 |
| 2,793,122 | 5/1957 | Erekson | 99/116 |
| 2,965,492 | 12/1960 | Bauman | 99/116 |
| 3,079,263 | 2/1963 | Foster et al. | 99/116 |
| 3,142,575 | 7/1964 | Tyman et al. | 99/116 |
| 3,156,568 | 11/1964 | Hargrove et al. | 99/116 |
| 3,172,767 | 3/1965 | Foster et al. | 99/116 |
| 3,175,915 | 3/1965 | Murphy | 99/116 |
| 3,295,991 | 1/1967 | Cort et al. | 99/116 |
| 3,359,116 | 12/1967 | Little | 99/54 |
| 3,375,118 | 3/1968 | Cox | 99/116 |
| 3,446,627 | 5/1969 | Noznick et al. | 99/115 |
| 3,650,768 | 3/1972 | Roberts | 99/116 |
| 3,667,968 | 6/1972 | Kasik et al. | 99/140 R |
| 3,689,286 | 9/1972 | Lukcas | 99/115 |
| 3,895,123 | 7/1975 | Moinas et al. | 426/534 |
| 3,975,544 | 8/1976 | Kosikowski | 426/35 |
| 4,119,732 | 10/1978 | Kratochvil | 426/36 |
| 4,172,900 | 10/1979 | Dooley | 426/38 |
| 4,244,971 | 1/1981 | Wargel et al. | 426/35 |
| 4,379,170 | 5/1983 | Hettinga et al. | 426/40 |
| 4,595,594 | 6/1986 | Lee et al. | 426/35 |

OTHER PUBLICATIONS

Schmidt et al, "Hydrolysis of Milk Proteins by Bacteria Used in Cheese Making," 1976, *J. Agric. Food Chem.*, 1108.

Wong et al, "Composition of Cheddar Cheese Made with Different Milk Clotting Enzymes," 1977, *J. Dairy Sci.*, 1522.

Sood and Kosikowski, "Ripening Changes and Flavor Development in Microbial Enzyme Treated Cheddar Cheese Slurries," 1979, *J. Food Sci.*, 1690.

*Primary Examiner*—Raymond N. Jones
*Assistant Examiner*—Marianne M. Cintins
*Attorney, Agent, or Firm*—Banner, Birch, McKie & Beckett

[57] ABSTRACT

A process for the rapid production of a flavored cheese ingredient wherein cheese curd is intimately combined with water, protease, and lipase to create a mixture, the temperature of the mixture is adjusted to between about 75° to 95° F., and the mixture is incubated for a time sufficient to produce a cheese-flavored ingredient. The invention also relates to the flavored cheese ingredient produced by this process, and to foods containing said ingredients.

20 Claims, No Drawings

METHOD FOR PRODUCING A HIGHLY FLAVORED CHEESE INGREDIENT

BACKGROUND OF THE INVENTION

1. Field of the Invention

This invention relates to highly flavored cheese ingredients intended to be partial or complete replacements for cheeses which have a sharp piccante flavor. This invention also relates to the method of producing these cheese ingredients, and to foods containing the ingredients.

2. Description of the Prior Art

The manufacture of natural cheese is well known in the art. Typically, milk is treated to increase its acidity. Various acid-producing micro-organisms for accomplishing this are well known in the art. Alternatively, lactic acid or another suitable edible acid can be added directly to the milk. Acidified milk is also known as ripened milk.

A clotting agent is added to the acidified milk, the temperature of the acidified milk is raised, or the milk is acidified beyond the iso-electric point to form a solid coagulum, also known as curd. Suitable clotting agents are rennet and other proteases. The curd then is separated from the remaining fluid (the whey) after a suitable period, the length of which is determined by the manufacturer. Whether the curd and whey are stirred before or during separation is a matter of choice. Typically, however, the curd must be agitated to some extent to allow for expulsion of whey from the curd matrix structure.

Various other organisms added to acidify the milk may also contribute to the flavor of the product. The optimum temperature for development of these organisms varies. Therefore, throughout the curd forming process, the temperature of the system may be adjusted to optimize conditions for curd formation.

After the desired incubation period and separation of curd from whey, the curd is placed in a vat so that additional whey can be removed. Typically, when a sufficient amount of whey has been removed so that the curd mats, i.e., the curd becomes sufficiently adherent, it is formed into blocks. If desired, further formation of acid is encouraged to achieve a specific flavor. For example, the curd can be "cheddared" by periodically (approximately every 15 minutes) turning the curd blocks over so that much of the whey is retained within the curd blocks for a longer period. Typically, cheddaring or simple drainage of whey from the curd blocks, as for American cheese, is stopped when the acidity of the draining whey, as measured by the pH, reaches the desired point.

When the curd blocks are sufficiently drained, they are milled and stirred and salt is added, whereupon additional whey is expelled. The salted curd then is placed in cloth-lined metal hoops or similar devices and subjected to pressure to form a cheese. This cheese can then be wrapped, coated, or otherwise protected. It is then stored under conditions of temperature and atmosphere appropriate for the type of cheese flavor desired.

Typically, a lengthy curing period at low (35°-50° F.) temperature, possibly under anaerobic conditions, is required to develop the flavor of the cheese. Generally, at least 60 days is required; one year is more typical. Thus, production of large quantities of naturally-aged cheese requires a substantial investment in appropriately regulated storage facilities. Therefore, various methods of producing cheese products which have the flavor of naturally-aged cheese but which do not require the lengthy aging period have been developed. These methods attempt to avoid the necessity of both the lengthy aging period and the forecasting of the demand for cheese one or more years in the future.

A method for developing cheddar flavored cheese products is disclosed in U.S. Pat. No. 3,689,286. After forming curd in a typical fashion, the curd is separated from the whey, preferrably is sterilized, and then is suspended in water. Sterilization is required if full flavor is to be developed. The suspension, which contains 5-50 percent solids is inoculated with micrococci and fermented, preferably aerobically, for 5-7 days with vigorous agitation. Agitation is said to be important to rapidly obtaining the desired flavor. The resultant product can be spray-dried to form a stable cheddar flavored concentrate.

A fluid ripening system is disclosed in U.S. Pat. No. 3,446,627, wherein sterilized milk is inoculated with desired bacteriological or mycological cultures after adjusting the solids concentration to between 9 and 50 percent in water. Alternatively, substantially unaged cheese curds can be macerated in water with the desired cultures. The fluid is incubated at conditions optimum for the growth of the culture for 2-10 days while being constantly agitated. When the desired flavor intensity has been achieved, the water is removed by pressing, evaporation, or another drying technique.

American cheese-flavored products can be produced by adding protease and lipase to conventionally prepared curds and aging the curds for a time sufficient to achieve fatty acid concentrations 10 times as great as those found in naturally aged cheese. According to U.S. Pat. No. 4,172,900, the amount of added protease, which could be the product "Rhozyme P-11", should be limited to 10 grams per 100 pounds curd to avoid production of a bitter taste. Further, the length of the aging period is a function of the temperature at which the curd is aged and preferably should be about 6 weeks. Shorter aging periods, which could be utilized if higher aging temperatures were maintained, are said to produce bitter flavor. This patent also discloses that unaged cheese curd blocks could be mixed with enzymes and optionally reformed into blocks for additional aging.

A process for producing a cheddar flavor product by adding lipase, protease, and optionally peptidase to cheddared cheese curds is disclosed in U.S. Pat. No. 3,975,544. Alternatively, but not preferably, the enzyme can be added to a previously prepared cheddar cheese. The treated curd or cheese then is aged for about one month until the desired flavor is developed.

The method disclosed in U.S. Pat. No. 4,119,732 requires the protease and lipase be added with the rennet or other suitable curd-forming proteolytic enzymes. The curd then may be cheddared and then is formed into the desired shape for aging. The flavor of a 9-12 month natural aging period is said to be developed in about 10 weeks at preferred temperatures. This flavor can be developed in 4-6 weeks at higher temperatures but the peak flavor will not be maintained in the product and an undesirable acid flavor will be produced.

A method for manufacturing cheese from milk from which the lactose has been removed or from a composition of liquid proteins, fats, and salts is disclosed in U.S. Pat. No. 4,379,170. Protein and fat fractions are treated with protease and lipase, respectively, to develop flavor before the curd is formed. These rapidly flavored fractions are then mixed with untreated fractions and curd is formed by adding a coagulant. Subsequent treatment depends upon the type of cheese desired. The aging period is variable; a cheddar cheese aged for 10 days is said to have the flavor of a cheese aged naturally for 4 months.

A different multiple-fraction technique for producing cheese products is disclosed in U.S. Pat. No. 4,244,971, wherein protein and fat concentrates are enzyme treated and mixed with untreated concentrates. Microorganisms required to produce the desired cheese flavor are added to the treated, highly digested fractions. This combination of treated and untreated fractions then is inoculated with a cheese starter culture, i.e., a microorganism which produces lactic acid. With this method, a cheese product purportedly can be produced in 24 hours.

None of these methods is an entirely satisfactory technique for quickly producing a cheese ingredient intended to be a partial or complete replacement for cheeses having sharp piccante flavor. The techniques in the prior art which produce cheese products in less than about 7 days require continuous agitation, yield products which are not useful unless dried, or require complex fractionation of milk or sources of protein- and fat-rich concentrates. Prior art techniques which yield a product useful in the form in which it is produced require an aging period of at least one month.

It is an object of this invention to quickly produce a highly flavored cheese ingredient which has a sharp piccante flavor.

It is a further object of this invention to quickly produce a highly flavored cheese ingredient intended to be a partial or complete replacement for cheeses which have a sharp piccante flavor.

SUMMARY OF THE INVENTION

In accordance with these and other objectives, this invention relates to a process for the rapid production of highly flavored cheese ingredients comprising the steps of combining a cheese curd with water, protease, and lipase to form a mixture, adjusting the temperature of said mixture to between about 75° to 95° F., and incubating the mixture for a time sufficient to produce a cheese-flavored ingredient.

This invention also relates to the highly flavored cheese ingredients produced by this process, and to foods containing the ingredients.

More particularly, this invention relates to the use in the process of cheddar-type or American-type cheese curd which is less than about 60 days old, and the highly flavored cheese ingredient produced by this process. The process using these "green" or unaged cheddar-type curds is described below, but the scope of the invention is not limited to this embodiment.

DETAILED DESCRIPTION OF THE INVENTION

Throughout the description and the claims, the word "milk" is deemed to include all forms of milk, such as but not limited to milk with reduced fats, whole milk, filled milk, reconstituted milk, recombined milk, cultured milk, and the like. Further, as used herein, "cheese products" and "cheese ingredients" refer to all solid or semi-solid foods prepared from milk curds, and should not be limited only to those products which meet the Standards of Identity described in 21 C.F.R. for Cheese and Cheese Products.

It has been discovered that a highly flavored cheese ingredient can be rapidly produced by combining "green" cheddar-type cheese curds with protease, lipase, and water, and incubating the mixture for a short period. The resulting highly flavored cheese ingredient has a sharp piccante flavor and is intended to be a partial or complete replacement for similarly flavored naturally prepared cheeses. Proteolytic components produce characteristics of aged cheese taste in the product.

The predominant component of the cheese ingredient is cheddar-type cheese curd. For purposes of this invention, curd of any age could be utilized. However, practical considerations limit the age of the cheddared curd to less than about 60 days. Cheese which has been aged longer can be sold as mild cheese and has developed a flavor of its own. Further, the cost of the cheese increases as the age increases. Therefore, cheddar-type curd which is less than about 60 days old is preferred.

In accordance with this invention, cheese curd is mixed with protease, lipase, and water. These components are blended thoroughly in any equipment suitable for the purpose of ensuring intimate contact between the enzymes and the curd particles. Grinding the cheese curd before it is mixed with the other ingredients is a particularly efficient method of ensuring intimate contact. Preferably, the curd is reduced to particles having a maximum diameter of 2 millimeters. Most preferably, no curd structure should be visible in the mixture. The aqueous mixture, which comprises a fairly uniform paste, encourages intimate contact between the enzymes and the cheese curd and encourages rapid flavor development.

Although the components can be admixed in any order, it is preferred to add the lipase and a substantial fraction of the water to the ground curd and to mix thoroughly. Then, the protease and the remaining water are added and the entire mass is mixed thoroughly. Cheese curd which is less than about 60 days old typically has a tough, rubbery consistency. Therefore, addition of the majority of the fluid facilitates the mixing of the enzymes into the curd. Further, this order of addition and thorough blending minimizes the possible deleterious effect the protease has on the lipase by ensuring that the local concentrations of each are minimized. Thus, the likelihood of destructive contact between the enzymes is minimized.

Lipase is an enzyme which is well-known in the art. Lipase are typically derived from the gullet tissues of young animals (calves, kids, or lambs), from the pancreas of adult animals, or from mycological sources. Various commercial preparations derived from gullet tissue are available from Dairyland Food, Marshall Laboratory, or other such companies under various trade names. The enzyme can be manufactured by grinding edible gullet with salt and non-fat dry milk, drying the mixture, and grinding again. The activity levels, as described below, can be adjusted by adding non-fat dry milk or salt to the mixture. Mycological sources of lipase are, e.g., the molds *Candida cylindracea*, Type VIII, *Aspergilus oryzae*, *A. niger*, *Penicillium roqueforti*, *P. glaucum*, and *Rhizopus oryzae*.

The amount of lipase to be used depends upon its activity. Lipase activity is measured in Lipase (forestomach) units (LFU), as described in *Food and Chemical Codex*, 3d Ed (1981) at page 493. One LFU releases 1.25 $\mu$mol of butyric acid per minute from a solution containing sodium casinate, hydroxylated lecithin, and tri-n-butyrin under test conditions fully described in the *Codex*. As is clear to those skilled in the art, 1 gram of lipase having an activity of 40 LFU's per gram has the same fat-digestive capability of 2 grams of lipase having an activity of 20 LFU's per gram.

In the practice of this invention an amount of lipase to provide between about 36,000 to 91,000 LFU's per 100 kilograms of curd, preferably between about 54,400 to 63,600 LFU's per 100 kilograms of curd, is added. The above described gullet/milk mixture is typically prepared to have an activity of 40 LFU's per gram of mixture. Therefore, between about 900 to 2,275, preferably between about 1,360 to 1,590, grams of this lipase mixture are required per 100 kilograms of curd. For the purposes of this invention, however, the precise activity level per gram is not critical. Thus, a lipase mixture having an activity of 400 LFU's per gram could be utilized. However, the amount required would be reduced by a factor of 10.

Protease is an enzyme which can be derived from fungal, plant, or animal sources, as is well-known in the art. For purposes of this invention, fungal protease is preferred. An example of such a fungal protease is a commercially available product called "Rhozyme P-11", sold by Genencor. This product has 10,000 casein solubilization units (CSU's) per gram. The manufacturer recites that an enzyme with activity of 1,000 casein solubilization units per gram solubilizes nine times its weight of casein in 1 hour at 40° C. and pH approximately 8, under conditions defined by the manufacturer. Other suitable proteases are Genencor's "Rhozyme P-53" and "Rhozyme P-54". Protease derived from plant and animal sources may also be acceptable.

Although other proteolytic enzymes may be used, the above-described proteases are preferred because they achieve the desired balance of reactions, minimizing the formation of bitter peptides while enhancing protein breakdown in the curd and completely hydrolysing some of the proteins to amino acids. Further, it has been discovered that too much protease causes bitter flavor to develop and that too little protease limits the development of the flavor, especially breakdown products which are similar to those in naturally aged cheeses.

In the method of this invention, an amount of protease should be added to supply between about 450,000 to 1,550,000, preferably between about 550,000 to 900,000, CSU's per 100 kilograms of curd. Thus, between about 45 to 155, preferably 55 to 90, grams of the preferred protease would be required per 100 kilograms of curd.

The preferred enzymes are all powders. However, suitable liquid forms of these enzymes would be acceptable for use in this invention. Indeed, in the preferred embodiment of the invention, powdered enzymes are separately admixed with water before being blended with the curd to ensure that they will be thoroughly distributed within the comminuted curd. The total quantity of water added should be between about 5 to 15 kilograms of water per 100 kilograms of curd. Preferably, the required amount of protease is dissolved in about 1 kilogram water per 100 kilogram curd, while the lipase is admixed with between about 9 to 10 kilograms of water per 100 kilograms of curd. Thus, the total mass of water added to the curd is preferably between about 10 to 11 kilograms per 100 kilograms of curd.

In the alternative, it is possible to utilize whey as a substitute for the water with which the enzymes are mixed. The traditional curd-formation process described above could be terminated by leaving between about 5 to 15 kilograms of whey per 100 kilograms of curd, preferably between about 10 to 11 kilograms of whey per 100 kilograms of curd, rather than completely draining the whey. In this embodiment, up to about 4 weight percent salt should be added in addition to the powdered enzymes. The liquid whey remaining with the curd substitutes for the water otherwise added with the enzymes, and allows intimate blending of the enzymes with the curd.

It has been discovered that the ratio of proteolytic enzyme strength to lipolytic enzyme strength affects the flavor of the product. To achieve a sharp piccante flavor, the ratio of proteolytic activity to lipolytic activity should be between about 5 to 43, preferably between about 8.5 to 10.5, CSU's per LFU. Ratios outside these ranges produce cheese-flavor different from the desired sharp piccante flavor, but would be useful should a different flavor be desired.

The blend must be incubated to develop the flavor desired. Various time/temperature relationships are possible, with shorter times requiring higher temperatures. It has been found that temperatures between about 75° to 95° F., preferably between about 82° to 90° F., and more preferably between about 86° to 88° F., yield the most desirable flavor without producing undue bitterness. It has been found that temperatures below about 75° F. are too low to allow flavor development to proceed at a commercially acceptable rate. Temperatures above about 95° F. tend to cause "oilout", i.e., separation of the fats from the curd, thereby degrading product quality.

Although achievement of the flavor desired is the best criterion for determining the adequacy of the incubation, this standard is both imprecise and commercially impractical. It has been discovered that the acid number is a reliable and commercially practical criterion for measuring the sufficiency of incubation. The acid number is the milligrams of KOH required to titrate, or neutralize, the free fatty acids in 1 gram of fat extracted from the product. A naturally aged cheddar cheese would have an acid number in the range of 3–6.

For rapidly-aged cheese products, the magnitude of the acid number is a rough indicator of the intensity of the flavor. It has been discovered that a rapidly aged cheese product with an acid number of 40 has approximately twice the flavor intensity of a similarly-prepared product having an acid number of 20.

It has been discovered that any acid number may be selected as the indicator of completion of flavor development, depending upon the intensity of flavor desired. However, to obtain a sharp piccante flavor, it is preferred to stop the incubation when the acid number is between about 15 to 50, more preferably between about 25 to 47, and most preferably between about 36 to 44.

Inadequate incubation will result in low acid numbers and will be reflected organoleptically by a lack of flavor. Excessive incubation results in bitter flavors. Neither situation produces commercially desirable product.

The acid number criteria should always be satisfied to ensure uniformity of result. Therefore, as can be appreciated by those skilled in the art, the length of the incubation period required to produce the desired flavor can be varied, with higher temperatures requiring less time. Between about 4 to 10 days can be required to achieve the desired flavors, but, if the most prefered temperature range of between about 86° to 88° F. is maintained, about 5 to 6 days is required to achieve the desired flavor.

An analytical method for measuring the degree of protein breakdown is the pH soluble nitrogen determination. This light adsorption analytical technique is well-known in the art, and is described in "A Rapid Spectrophotometric Method for Measuring Cheese Ripening." 42 *J. Dairy Sci.* 264–276 (1959). It has been discovered that the preferred embodiment of this invention yields a pH 4.6 soluble nitrogen essentially equal to that of naturally-aged cheese.

The highly flavored cheese ingredient of this invention is a plastic solid which can be used directly in various products, such as sauces and processed cheese blends. The ingredient can be blended with less-intensely flavored convenionally-prepared cheeses which have been aged for less than 3 months. The resulting product would have an enhanced cheese flavor.

Adjuvants such as other cheese flavors, fillers, dyes, pigments, spices, monosodium glutamate, vitamins, phosphates, and other ingredients known to those who produce cheese products can be added. After all the adjuvants have been blended, the cheese ingredient preferably is cooled to a temperature of about 35° F. and stored. If storage of longer than two weeks is anticipated, the cheese ingredient can be frozen at temperatures below about −10° F.

Various modes of use or storage can be utilized. The cheese ingredient can then be pumped or gravity filled into sterile plastic pails, bottles, or bags or any other appropriate container. Alternatively, the product can be dried by any method. For example, spray drying is acceptable, although the dried powder would have a slightly toasted taste. The cheese ingredient of the method of this invention can be used in any product where a cheese or cheese flavoring is typically used. Its use is not limited to human foods. This cheese product can also be used in animal foods such as dog food, cat food, and the like.

Typically, however, the highly flavored cheese ingredient is used in sauces and other cheese products such as cheese spreads, snack foods, salad dressings and processed cheese foods. It can be used with pasta products such as macaroni and cheese or it can be used to enhance the flavor of soups, stews, and casseroles, which can be made with conventional ingredients.

The following examples further illustrate the methods of the invention.

EXAMPLE 1

An American-type cheese curd aged less than 60 days was warmed to about 70° F. and ground to reduce the curd to particles less than about 2 millimeters in diameter. A lipase mixture containing an amount of whole calf gullet ground with an equal amount of non-fat dry milk plus 2.5 pounds of sodium chloride per 100 pounds of milk/gullet mixture was prepared. The lipase mixture was dried and the activity was adjusted to 40 LFU's per gram of mixture.

Four-and-one-half pounds of this lipase mixture was mixed into 29 pounds of water and allowed to rehydrate for 30 minutes. This solution was then poured over 300 pounds of ground curd and thoroughly blended for five minutes to produced a smooth paste.

Fifty-nine grams of proteolytic enzyme "Rhozyme P-11" was dissolved in 1 kilogram of water and blended into the paste. After the temperature of the paste was adjusted to between about 86° to 88° F., the paste was incubated for 5 and ½ days. The acid number at this time was 42. The cheese ingredient was then discharged into containers and chilled to 35° F. for storage.

The highly flavored cheese ingredient was organoleptically pleasing, having a smooth texture and a sharp flavor.

EXAMPLE 2

A cheese sauce containing a sauce base, aged Cheddar Cheese, and a product of this invention, was found to be organoleptically pleasing. The sauce base was a mixture of water with primarily modified food starch, butter, and acid whey powder, with a minor amount of salt.

EXAMPLE 3

The sauce of example 2 is used as the sauce for a macaroni and cheese dish. The cheese dish is found to be organoleptically pleasing.

EXAMPLE 4

The product of this invention was substituted for one-half of the Romano and Parmesan cheeses in a minestrone soup. The soup was primarily beef stock, pasta, vegetables, and cheeses, with minor amounts of adjuvants. The soup was organoleptically pleasing.

EXAMPLE 5

The product of this invention was substituted for one-half of the Romano and Parmesan cheeses utilized in a garnish for a French Onion soup. The garnish was found to be organoleptically pleasing.

Although preferred embodiments of this invention have been discussed herein, those skilled in the art will appreciate that changes and modifications may be made without departing from the spirit of this invention as defined in and limited only by the scope of the appended claims.

We claim:

1. A process for producing a flavored cheese ingredient comprising:
   a. forming a mixture by combining ingredients consisting essentially of a cheese curd with water, protease in an amount to provide at least about 450,000 CSU's per 100 kilograms of curd, and lipase in an amount to provide at least about 36,000 LFU's per 100 kilograms of curd;
   b. adjusting the temperature of said mixture to between about 75° to 95° F.; and
   c. incubating said mixture at said temperature for a time sufficient to produce a flavored cheese ingredient.

2. The process of claim 1 wherein the cheese curd is cheddar-type or American-type curd.

3. The process of claim 1 wherein the cheese curd is ground before the mixture is created.

4. The process of claim 1 wherein the mixture is a smooth paste.

5. The process of claim 1 wherein protease in an amount to provide between about 450,000 to 1,550,000 CSU's per 100 kilograms of curd is added.

6. The process of claim 5 wherein protease in an amount to provide between about 550,000 to 900,000 CSU's per 100 kilograms of curd is added.

7. The process of claim 1 wherein lipase in an amount to provide between about 36,000 to 91,000 LFU's per 100 kilograms of curd is added.

8. The process of claim 7 wherein lipase in an amount to provide between about 54,500 to 63,600 LFU's per 100 kilograms of curd is added.

9. The process of claim 1 wherein between about 5 to 15 kilograms of water are added per 100 kilograms of curd.

10. The process of claim 1 wherein the length of the incubation of step (c) is between about 4 to 10 days.

11. The process of claim 10 wherein the length of the incubation of step (c) is between about 5 to 6 days.

12. The process of claim 6 wherein said temperature of the mixture is between about 82° to 90° F.

13. The process of claim 1 wherein said temperature of the mixture is between about 86° to 88° F.

14. The process of claim 1 wherein the lipase and a major portion of the water are first thoroughly blended into the curd, after which the protease and the remaining portion of the water are added.

15. A process for producing a flavored cheese ingredient comprising:
   a. forming a mixture by intimately ingredients consisting essentially combining cheddar-type or American-type cheese curd with from about 10 to 11 kilograms of water per 100 kilograms of curd, with protease in an amount to provide between about 550,000 to 900,000 CSU's per 100 kilograms of curd, and with lipase in an amount to provide between about 54,500 to 63,600 LFU's per 100 kilograms of curd;
   b. adjusting the temperature of said mixture to between about 82° to 90° F.; and
   c. incubating said mixture at said temperature for between about 5 to 6 days to produce a flavored cheese product.

16. The process of claim 15 wherein the lipase and a major portion of the water are first thoroughly blended into the curd, after which the protease and the remaining portion of the water are added.

17. A process for producing a flavored cheese ingredient comprising:
   a. providing a mixture of cheese curd and whey, said mixture containing between about 5 to 15 kilograms of whey per 100 kilograms of curd;
   b. intimately combining with said cheese curd and whey protease in an amount to provide at least about 450,000 CSU's per 100 kilograms of curd and lipase in an amount to provide at least about 36,000 LFU's per 100 kilograms of curds thereby forming a mixture consisting essentially of cheese curd, whey, protease and lipase;
   c. adjusting the temperature of said mixture of step (b) to between about 75° to 95° F.; and
   d. incubating said mixture at said temperature for a time sufficient to produce a flavored cheese ingredient.

18. The process of claim 17 wherein protease in an amount to provide between about 550,000 to 900,000 CSU's per 100 kilograms of curd and lipase in an amount to provide between about 54,500 to 63,600 LFU's per 100 kilograms of curd are added.

19. The process of claim 18 wherein said temperature is between about 82° to 90° F.

20. The process of claim 18 wherein the length of the incubation of step (d) is between about 4 to 10 days.

* * * * *